United States Patent [19]

Mitsuhashi et al.

[11] 4,320,120
[45] Mar. 16, 1982

[54] **EXTRACTS OF *MARSDENIA CUNDURANGO* REICHENBACH FIL**

[75] Inventors: Hiroshi Mitsuhashi, Sapporo; Den-ichi Mizuno, Kamakura; Koji Hayashi, Sapporo; Shigeru Abe, Tokyo; Muneaki Takase, Oizumimachi; Toshiharu Narita, Higashimurayama, all of Japan

[73] Assignee: Zenyaku Kogyo Kabushiki Kaisha, Tokyo, Japan

[21] Appl. No.: 179,001

[22] Filed: Aug. 18, 1980

[30] Foreign Application Priority Data

Oct. 22, 1979 [JP] Japan .................. 54-136061
Mar. 5, 1980 [JP] Japan .................. 55-27696
Mar. 5, 1980 [JP] Japan .................. 55-27697
Apr. 19, 1980 [JP] Japan .................. 55-52097

[51] Int. Cl.$^3$ .................. A61K 31/705; A61K 35/78
[52] U.S. Cl. .................. 424/182; 424/195
[58] Field of Search .................. 424/195, 182

[56] References Cited

U.S. PATENT DOCUMENTS 116530 0/1871 Baker .................. 424/195

OTHER PUBLICATIONS

Koji et al., Chemical Abstracts, vol. 93:204968b, (1980), citing Chem. Pharm. Bull. 1980, 28(6), pp. 1954–1958.
Remington, The Practice of Pharmacy, 3rd Ed., (1895), published by J. B. Lippincott Co., Phil., p. 950.
The Dispensatory of U.S.A., 24th Ed. (1947), published by J. B. Lippincott Co., Phil., pp. 1409 & 1410.

*Primary Examiner*—Donald B. Moyer
*Attorney, Agent, or Firm*—Browdy and Neimark

[57] ABSTRACT

New extracts of *Marsdenia cundurango* Reichenbach fil., processes for preparing them, antitumor agents comprising them, compositions containing them and methods of treating tumor with them are described herein in which the extracts consist essentially of the portion of *Marsdenia cundurango* Reichenbach fil. which is soluble in lower alcohols and in chlorinated hydrocarbons other than carbon tetrachloride and insoluble in carbon tetrachloride or aromatic hydrocarbons.

13 Claims, 20 Drawing Figures

EXTRACTS OF *MARSDENIA CUNDURANGO* REICHENBACH FIL

The present invention relates to extracts of *Marsdenia cundurango* Reichenbach fil., processes for preparing them, antitumor agents comprising them, compositions containing them and methods of treating tumor with them.

*Marsdenia cundurango* Reichenback fil. belonging to the family Asclepiadaceae is a shrub of somewhat winding type growing natually on and between mountains in the northwest of South America. Its bark is employed as an aromatic but bitter stomachic at the time of digestive disorder and/or anorexia, usually in the form of fluid extract (Commentary for the ninth Japanese Pharmacopeia).

The components of the bark of *Marsdenia cundurango* Reichenback fil. include condurangogenin-A, condurangogenin-C and many other pregnane type compounds and their esters and glycosides, and the extraction, separation, structures and so on of them have been reported in, for example, the following documents. But, their details are still unclear in many points.

R. Tschesche et al., Tetrahedron, 21, p. 1777 (1965); and 21, p. 1797 (1965); 23, p. 1461 (1967); and 24, p. 4359 (1968).

M. Pailer et al., Monatshefte für Chemie, 106, p. 37 (1975).

Hiroshi Mitsuhashi et al., Chem. Pharm. Bull., 16, p. 2522 (1968).

As a result of their study, the inventors of the present invention have found that certain extracts of *Marsdenia cundurango* Reichenback fil. and certain elution fractions obtained by subjecting the extracts to high pressure liquid chromatography (hereunder referred to as HPLC) have antitumor activity. Thus, the present invention has been completed.

Hereunder, the present invention will be explained in detail.

In carrying out the present invention, the bark of *Marsdenia cundurango* Reichenbach fil. is preferred. This bark may be a commercially available one, but it is preferably one well dried and finely divided soon after its collection.

In view of the nature of the preparation of extracts, the order of the use of solvents is also not critical in carrying out the present invention, and it may be changed according to convenience. A preferred embodiment of the process of the present invention is as follows:

(First operation)

*Marsdenia cundurango* Reichenback fil., for example, its bark, is finely divided and extracted with an organic solvent, and the extract is concentrated to dryness under reduced pressure. As the organic solvent, methanol, ethanol, isopropanol or any other lower alcohols may be employed, but methanol is preferred.

Here, prior to the extraction, *Marsdenia cundurango* Reichenback fil. may be defatted with an aliphatic hydrocarbon such as pentane, hexane, heptane, ligroine or petroleum ether. This pre-treatment is preferably effected using hexane in an amount 4–7 times (v/w) that of *Marsdenia cundurango* Reichenbach fil..

In an embodiment of this extraction operation, the extraction is effected by allowing the starting material-solvent mixture to stand at room temperature for from several to several tens of hours. Then, the mixture is filtered to yield a filtrate. The residue is subjected to the same extraction-filtration as the above repeatedly, and all the filtrates are combined and concentrated to dryness under reduced pressure to yield an extract.

The extraction is usually effected at normal temperatures, but may be effected while heating in order to shorten the extraction time. This extraction with heating is preferably carried out on a water bath at a water bath temperature of 35°–55° C. for 4–6 hours using a reflux condenser. It may be effected according to the percolation method.

The amount of the solvent used is 2–5 times (v/w) that of *Marsdenia cundurango* Reichenback fil. The extraction residue is preferably subjected to extraction under the same conditions as the above three or more times using the solvent in an amount 0.4–0.8 times (v/v) that of the solvent first used.

The separation may be conducted by paper filtration, centrifugation or the like. Better results are given by conducting the separation by suction filtration using commercially available filtration aids, for example, Radiolite (Showa Chemical Industry Co., Ltd. in Japan), Celite (Wako Junyaku Industry Co., Ltd. In Japan), Fibra Cel (Johns Manville Co., Ltd. in U.S.), etc.

The reduction in pressure is conducted in a usual manner, for example, using an aspirator, vacuum pump or the like.

As the extraction vessel, one with a glass-lined or enameled inner surface or one made of stainless steel is employed.

(Second operation)

To the extract obtained by first operation, there is added a chlorinated hydrocarbon other than carbon tetrachloride, such as chloroform or dichloromethane, followed by vigorous shaking to remove the insoluble portion. The insoluble portion is subjected to the same operation as the above repeatedly. All the remaining solutions are combined and concentrated to dryness under reduced pressure directly or after suction filtration. The amount of the solvent used is 2–6 times (v/w) that of the extract obtained by the first operation. The respective residues are preferably subjected to the same operation as the above four or five times, but using the solvent in an amount 0.2–0.4 times (v/v) that of the solvent first used.

The suction filtration may be carried out in the same manner as in the first operation.

(Third operation)

The extract obtained by the second operation is dissolved in a chlorinated hydrocarbon other than carbon tetrachloride such as chloroform or dichloromethane, in the minimum amount necessary to dissolve the former completely. To the resulting solution, there is added an aliphatic hydrocarbon such as pentane, n-hexane or heptane in an amount two to four times (v/v) that of the former followed by well stirring and allowing to stand for from several to several tens of hours to collect the insoluble portion. Alternatively, carbon tetrachloride or an aromatic hydrocarbon such as toluene or benzene may be added to the extract directly in amount the same as or up to three times (v/w) that of the latter and then be worked up as in the above to collect the insoluble portion.

The insoluble portion is subjected to the same operation as the above repeatedly. This operation is preferably conducted two or three times, each time using the solvent in an amount 0.4–0.6 times (v/v) that of the solvent first used. The thus obtained insoluble portion is well dried at a temperature of 50° C. or less under reduced pressure and crushed to yield a brown powder-like extract (hereunder referred to as Extract A). The collection of the insoluble portion may be made by decantation, suction filtration or centrifugation with advantage. In order to lower the total cost of the process of the present invention and to make the operation easier to follow, finely divided Marsdenia cundurango Reichenbach fil., for example, its bark, may first be extracted with an aliphatic ketone such as acetone or methyl ethyl ketone, a lower aliphatic ester such as methyl acetate, ethyl acetate or butyl acetate, an ether such as diethyl ether, tetrahydrofuran or dioxane or hot water or be treated with heat (110°–130° C. for 30 min. or more) directly followed by the extraction with water or an aqueous lower alcohol, and then the extract may be subjected to the above mentioned three operations. Here, the extraction may be carried out in the same manner as in the above first operation. Usually, β-glycosidase capable of breaking glucose linkages of glycosides is present in extracts of plants, and this enzyme is activated in the presence of water. For this reason, the treatment with heat is required when water or an aqueous lower alcohol is used. The thus obtained Extract A is a mixture of six components showing characteristic peaks in the chromatograms depicted in FIGS. 1, 8 and 12–20 of the accompanying drawings when subjected to analytical HPLC, and has antitumor activity.

(Fourth operation)

In order to obtain a more active portion from Extract A, it is dissolved in chloroform in the minimum amount necessary for the complete dissolution of it, and to the resulting solution there is added n-hexane in such an amount that the solution does not become turbid. The obtained sample is subjected to normal phase HPLC for mass collection [eluant: a mixture of n-hexane/chloroform/methanol (volumetric ratio=6:3:1)]. While observing elution peaks with a detector, two fractions chosen on the basis of the peaks corresponding to Fr-2 and Fr-3 fractions depicted in the chromatogram (FIG. 2 of the accompanying drawings) obtained beforehand by preliminary tests are collected, respectively, and then each is concentrated to dryness to yield extracts.

Alternatively, Extract A obtained by the third operation may be subjected to the open column method eluting successively with chloroform and mixtures of chloroform and methanol (volumetric ratio: 97:3-95:5) to remove the lesser polar portion, and then eluting with a mixture of chloroform and methanol (volumetric ratio=93:7) to yield after concentration to dryness, two fractions corresponding to Fr-2 and Fr-3 fractions mentioned above. Here, usually the first half of the eluate corresponds to Fr-2 fraction, and the latter half, to Fr-3 fraction, but the volumetric ratio of the two fractions is desired to be 60:40.

Next, the extract corresponding to Fr-2 fraction is, as mentioned above, subjected to normal phase HPLC for mass collection [eluant: a mixture of n-hexane/chloroform/methanol (volumetric ratio=6:1:1)]. While observing elution peaks with a detector, fractions chosen on the basis of the peaks corresponding to Fr-2-1 and Fr-2-2 fractions depicted in the chart (FIG. 3 of the accompanying drawings) obtained beforehand by preliminary tests are collected, respectively, and each is concentrated to dryness to yield white powder-like extracts (hereunder referred to as Extract B-1 and Extract B-2).

On the other hand, the extract corresponding to Fr-3 fraction is subjected to reversed phase HPLC for mass collection (eluant: a 65–75% (v/v) aqueous methanol solution). While observing elution peaks with a detector, fractions chosen on the basis of the peak corresponding to Fr-3-1 fraction depicted in the chart (FIG. 6 of the accompanying drawings) obtained beforehand by preliminary tests are collected and concentrated to dryness to yield a white powder-like extract (hereunder referred to as Extract B-3).

The thus obtained extracts of the present invention have the following characteristic aspects.

1. Properties:
   (1) Extract A is a brown powder while Extracts B-1, B-2 and B-3 are white powders. All of them taste bitter and give out a cinnamic acid-like odor when a caustic soda solution is added thereto followed by heating.
   (2) Solubility (Extracts A, B-1, B-2 and B-3)
   Soluble in lower alcohols and in chlorinated hydrocarbons other than carbon tetrachloride.
   Insoluble in aliphatic hydrocarbons, carbon tetrachloride or aromatic hydrocarbons.
2. U. V. spectra (Extracts A, B-1, B-2 and B-3)
   $\lambda$ max=280 nm (in methanol)
3. Mass spectra (Extracts A, B-1, B-2 and B-3)
   Show a base peak of cinnamoyl cation at $m/e=131$ and an ion peak of acetyl cation at $m/e=43$.
   Thus, the presence of cinnamic and acetic esters in the extracts is suggested.
4. Liquid chromatography
   (Conditions)
   Filler: silica gel (Wako-gel LC-5H-totally porous crushed type, 5$\mu$, manufactured by Wako Junyaku Industry Co., Ltd. in Japan)
   Colunn: i.d.×1.=4 mm×200 mm
   Eluant: a mixture of n-hexane/chloroform/methanol (volumetric ratio=7:2:1)
   Flow rate: 1.5 ml/min.
   Pressure: 30 Kg/cm$^2$
   Detection: at U.V. 280 nm (0.64 AUFS)
   Under the above conditions, 20 mg of each of Extracts A, B-1, B-2 and B-3 dissolved in 10 ml of chloroform is subjected to liquid chromatography. The obtained characteristic chromatogram are shown in FIGS. 1, 4, 5 and 7 of the accompanying drawings (they reflect data obtained on Extracts A, B-1 and B-2 prepared in Example 1 and Extract B-3 prepared in Example 2, respectively).

In the accompanying drawings.

5. Color reaction (Extracts A, B-1, B-2 and B-3)

Keller Kiliani reaction [Helvetica Chimica Acta., 31, p. 883 (1948)]: Positive (greenish brown)

Liebermann Burchard reaction [Iwanami's Dictionary of Physics and Chemistry, 3rd edition p. 1411 (1977), issued in Japan]: Positive (blueish green)

Thus, the extracts are supposed to consist mainly of steroid glycosides having 2, 6-deoxysugars.

The antitumor activity of the extracts of the present invention were confirmed by the screening test mentioned below.

Two type tumors, Sarcoma-180 and *Ehrlich carcinoma*, were employed in the evaluation of the antitumor properties, and the tested tumors were of subcutaneous tubercle type.

The group to which the extracts of the present invention were administered consisted of seven mice while the control group consisted of ten mice.

Test method (1) Sarcoma-180

The experimental animals were six week old ICR male mice (body weight: 30–32 g).

The tumors were translated intraperitoneally into the mice. On the seventh day after the transplantation, the well grown cells of the tumors were taken out, and $4 \times 10^6$ cells of them were transplanted subcutaneously in the inguinal region of the mice to form solid tumors. At and after 24 hours after the transplantation, the extracts of the present invention dissolved in physiological saline solutions were administered to the mice intraperitoneally.

The volume of the respective solutions administered was 0.2 ml per mouse at one time and the administration was conducted for ten days at a rate of one time per day. Only physiological saline solutions were given to the mice of the control group.

On the thirtieth day after the transplantation, the tumors were taken out to measure the average weight of the tumors of the mice of the group to which the extracts of the present invention had been administered (T) and that of the control group (C) to calculate the T/C (%).

(2) Ehrlich carcinoma

The experimental animals were six week old ddY male mice (body weight: 28–30 g)

The tumors were transplanted intraperitoneally the mice. On the seventh day after the transplantation, the well grown cells of the tumors were taken out, and $1.5 \times 10^6$ cells thereof were transplanted subcutaneously into the inguinal region of the mice to form solid tumors, and then worked up as in the case of the Sarcoma-180 to calculate the T/C (%).

| Extract | Dose (mg/kg × times) | T/C (%) Ehrlich carcinoma | Sarorma-180 |
|---|---|---|---|
| Extr. A of Ex. 1 | 40 × 10 | 34.1 | 15.2 |
| Extr. B-1 of Ex. 1 | 15 × 10 | 24.3 | 13.6 |
| Extr. B-2 of Ex. 1 | " | 29.8 | 5.0 |
| Extr. B-3 of Ex. 2 | " | 31.0 | 20.0 |
| Extr. B-1 of Ex. 3 | " | 18.0 | 8.2 |
| Extr. B-2 of Ex. 3 | " | 21.0 | 4.7 |
| Extr. B-3 of Ex. 4 | " | 30.3 | 15.2 |
| Extr. A of Ex. 5 | 40 × 10 | 13.5 | 19.8 |
| Extr. A of Ex. 6 | " | 15.0 | 39.8 |
| Extr. A of Ex. 7 | " | 22.8 | 26.6 |
| Extr. A of Ex. 8 | " | 32.1 | 40.0 |
| Extr. A of Ex. 9 | " | 30.5 | 32.7 |
| Extr. A of Ex. 10 | " | 40.3 | 28.4 |
| Extr. A of Ex. 11 | " | 30.0 | 22.2 |
| Extr. A of Ex. 13 | " | 23.1 | 19.0 |

Next, the extracts of the present invention were administered to five week old ddY male mice (body weight: 21–25 g) intraperitoneally to determine the acute toxic values ($LD_{50}$).

Results

| Extract | $LD_{50}$(mg/kg) |
|---|---|
| Extr. A of Ex. 1 | 400 |
| Extr. B-1 of Ex. 1 | 610 |
| Extr. B-2 of Ex. 1 | 78 |
| Extr. B-3 of Ex. 2 | 382 |
| Extr. B-1 of Ex. 3 | 608 |
| Extr. B-2 of Ex. 3 | 80 |
| Extr. B-3 of Ex. 4 | 370 |
| Extr. A of Ex. 5 | 415 |
| Extr. A of Ex. 6 | 350 |
| Extr. A of Ex. 7 | 383 |
| Extr. A of Ex. 9 | 398 |
| Extr. A of Ex. 11 | 400 |

The extracts of the present invention may be administered to human body orally, by injection (intravenously, subcutaneously or intramuscularly) or in any other manner.

When the extracts of the present invention are employed in the form of solid preparations for oral administration, the preparations may be tablets, granules, powders, capsules or the like. The preparations may contain additives, for example, an excipient such as a saccharide or cellulose preparation, a binder such as starch paste or methyl cellulose, a filler, a disintegrator and so on, all being ones usually used in the manufacture of medical preparations. In case the extracts of the present invention are employed as oral liquid preparations, they may be of any form selected from aqueous preparations for internal use, suspensions, emulsions, syrups, etc., and further they may be in the form of dried products which are dissolved prior to the use.

When the extracts of the present invention are orally administered to adults, they may be employed in a dose of 3.0–30.0 mg/kg (Extract A), 1.2–48.0 mg/kg (Extract B-1), 1.2–6.0 mg/kg (Extract B-2) or 1.2–30.0 mg/kg (Extract B-3) per day. Here, of course, the dose may be increased or decreased appropriately depending on the conditions of disease, the age of the patient, the form of the preparation administered, etc.

The extracts of the present invention may be injected in the form of aqueous solutions, suspensions or oily or aqueous emulsions, but usually the injections are prepared by dissolving or suspending them in aqueous liquid media such as sterile water of physiological saline solutions. If necessary, conventionally used dissolving agents, stabilizers, preservatives, additives for preparing isotonic solutions, etc. may be added to the injections.

The thus obtained injection preparations are administered intravenously, intramuscularly, subcutaneously or in any other appropriate manner. When the injections are administered to adults parenterally, they may contain 1.0–10.0 mg/kg of Extract A, 0.4–16.0 mg/kg of Extract B-1, 0.4–2.0 mg/kg of Extract B-2 or 0.4–10.0 mg/kg of Extract B-3 per day. Of course, this dose level is increased or decreased appropriately depending on the conditions of disease, the age of the patient, the form of the preparation administered, the administration manner and so on.

Hereunder, the present invention will be explained in detail with reference to examples given below.

EXAMPLE 1

One liter of methanol was added to 500 g of finely divided bark of *Marsdenia cundurango* Reichenbach fil., and the mixture was allowed to stand at room temperature overnight. Then, the mixture was filtered, and the residue was further treated three times in the same manner as the above, each time using 0.75 l of methanol.

All the filtrates were combined, and then concentrated to dryness at 45° C. under reduced pressure to yield 69 g of an extract. To this extract transferred into a separatory funnel, there was added 150 ml of chloroform followed by vigorous shaking, and then the chloroform layer was obtained. To the residue, there was added 50 ml of chloroform to repeat the same operation as the above three times. All the chloroform extracts were combined and then subjected to suction filtration using Fibra Cel BH-40 (Johns Manville Co., Ltd.) as the filtration aid. The resulting filtrate was concentrated to dryness at 40° C. under reduced pressure to yield 42 g of an extract. This extract was dissolved in 50 ml of chloroform added thereto followed by the addition of 100 ml of n-hexane. The resulting mixture was well stirred and allowed to stand for 12 hours. Then, it was subjected to decantation to obtain the insoluble portion. This portion was dissolved in 25 ml of chloroform followed by the addition of 50 ml of n-hexane, and the solution was well stirred and allowed to stand for 2 hours. The solution was subjected to decantation to obtain the insoluble portion and then treated in the same manner as in the above three times. The finally obtained insoluble portion was dried at 45° C. under reduced pressure for 6 hours and crushed to yield 18 g of a brown powder-like Extract A.

The thus prepared 20 mg of the Extract A was dissolved in 10 ml of chloroform, and the resulting solution was subjected to analytical HPLC [filler: silica gel (Wako-gel LC-5H, manufactured by Wako Junyaku Industry Co., Ltd., totally porous crushed type, $5\mu$); column: i.d.×1.=4 mm×200 mm; eluant: a mixture of n-hexane/chloroform/methanol (volumetric ratio=7:2:1); flow rate: 1.5 ml/min.; pressure: 30 kg/cm$^2$; and detection: at U.V. 280 nm (0.64 AUFS)]. The obtained data is shown in the chromatogram depicted in FIG. 1 of the accompanying drawings.

Then, the Extract A (6 g) was dissolved in 50 ml of chloroform. Then, n-hexane was added to the resulting mixture in the maximum but no turbidity-causing amount, and the resulting solution was subjected to HPLC for mass collection [System 500 manufactured by Waters Co., Ltd., filler: Preppak 500-Silica (manufactured by Waters Co., Ltd., totally porous silica gel, spherical, surface area=320 m$^2$/g); column: i.d.×1.=57 mm×300 mm, each contains 325 g of the filler; eluant: a mixture of n-hexane/chloroform/methanol (volumetric ratio=6:3:1); flow rate: 150 ml/min.; and detection: at RI ($1/20×10^{-4}$ RIUFS)]. While observing elution peaks with a detector, an eluate chosen on the basis of the peak corresponding to Fr-2 fraction shown in FIG. 2 of the accompanying drawings was collected for 12 minutes. The foregoing operation was repeated two more times, each time using fresh 6 g of the Extract A. All the eluates were combined and concentrated to dryness at 40° C. to yield 5.54 g of an extract. This extract was dissolved in 50 ml of chloroform followed by the addition of n-hexane in the maximum but no turbidity-causing amount. The resulting solution was then subjected to HPLC under the same conditions as the above except that a mixture of n-haxane/chloroform/methanol (volumetric ratio=6:1:1) was used as the eluant. While observing elution peaks with a detector, an eluate chosen on the basis of the peak corresponding to Fr-2-1 fraction shown in FIG. 3 of the accompanying drawings was collected for six minutes and thirty seconds, and separately another eluate chosen on the basis of the peak corresponding to Fr-2-2 fraction shown in the same chart was collected for 8 minutes.

The respective fractions were concentrated to dryness to yield 1.98 g of a white powder-like Extract B-1 (corres. to Fr-2-1 fraction) and 0.91 g of a white powder-like Extract B-2 (corres. to Fr-2-2 fraction).

The data obtained by subjecting the thus obtained Extracts B-1 and B-2 to HPLC under the same conditions as in the case of the Extract A mentioned above, respectively, is shown in FIGS. 4 and 5 of the accompanying drawings, respectively.

EXAMPLE 2

Figure 1:
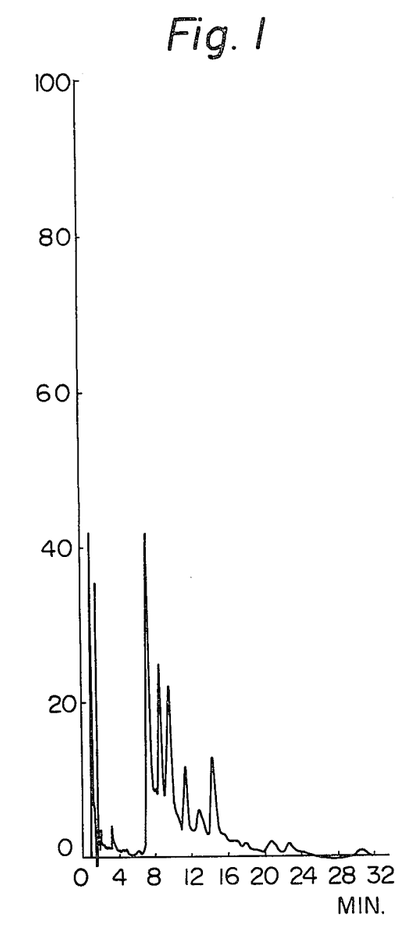
FIG. 1 shows a chromatogram obtained by subjecting the Extract A obtained in Example 1 to analytical HPLC.
Figure 2:
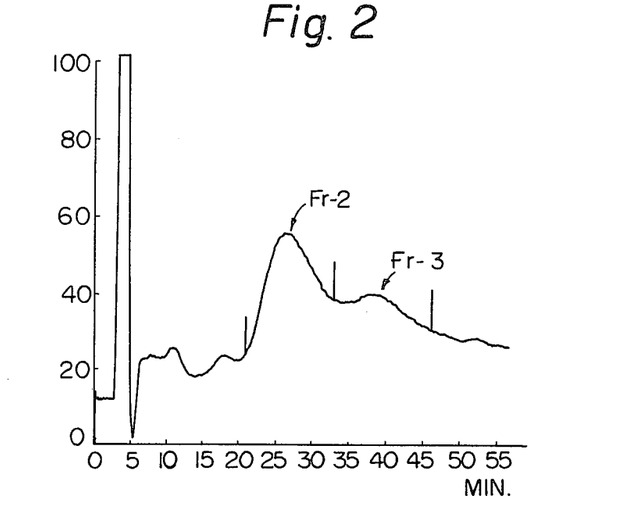
FIG. 2 shows a chromatogram obtained by subjecting the Extract A obtained in Example 1 to HPLC for mass collection.

An eluate from the first HPLC for mass collection in Example 1 collected for 13 minutes on the basis of the peak corresponding to Fr-3 fraction depicted in FIG. 2 of the accompanying drawings was concentrated to dryness at 40° C. to yield 2.88 g of an extract. This extract was dissolved in a 70% (v/v) aqueous methanol solution and then subjected to HPLC for mass collection [System 500 manufactured by Waters Co., Ltd.; filler: Preppak 500-C18 (manufactured by Waters Co., Ltd., chemically bonded type C-18); column: i.d.×1.=57 mm×300 mm; eluant: a 70% (v/v) aqueous methanol solution; flow rate: 100 ml/min.; and detection: at RI ($1/50\times10^{-4}$ RIUFS)].

Figures 5, 6:
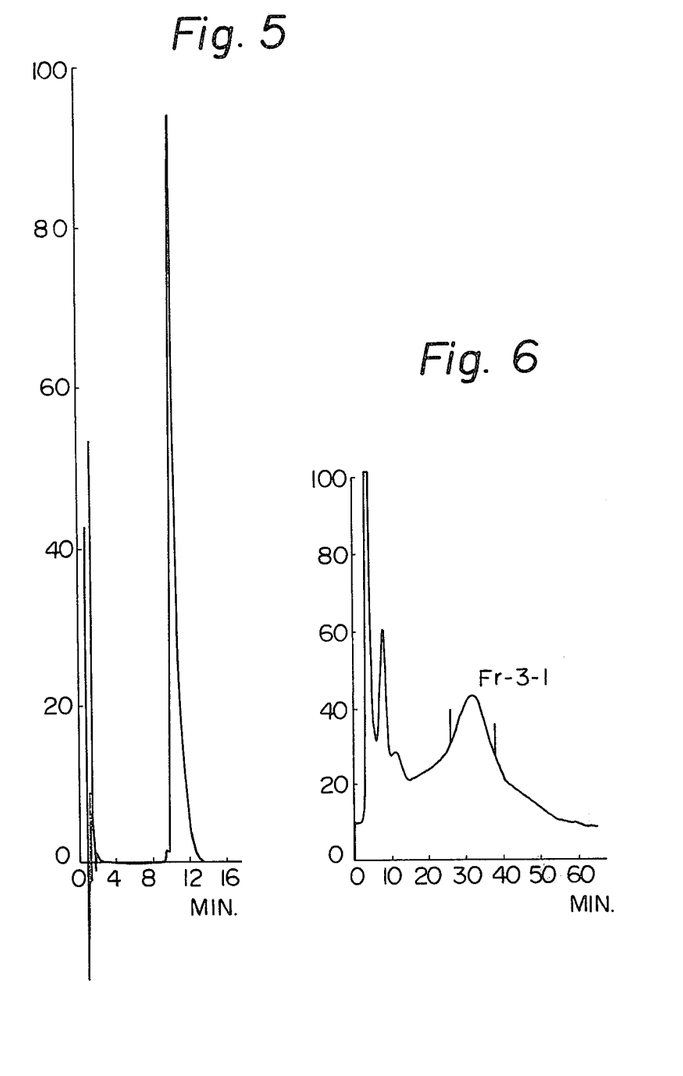
FIG. 5 shows a chromatogram obtained by subjecting the Extract B-2 obtained in Example 1 to analytical HPLC.
FIG. 6 shows a chromatogram obtained by subjecting the Fr-3 fraction depicted in FIG. 2 to HPLC for mass collection.
Figure 7:
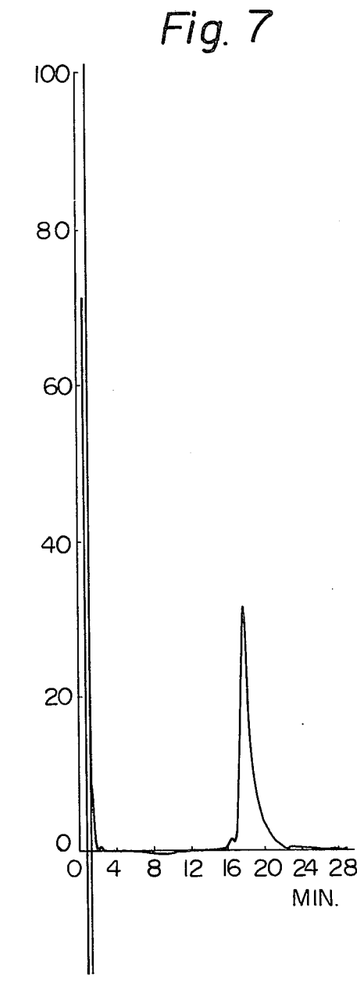
FIG. 7 shows a chromatogram obtained by subjecting the Extract B-3 obtained in Example 2 to analytical HPLC.
Figure 8:
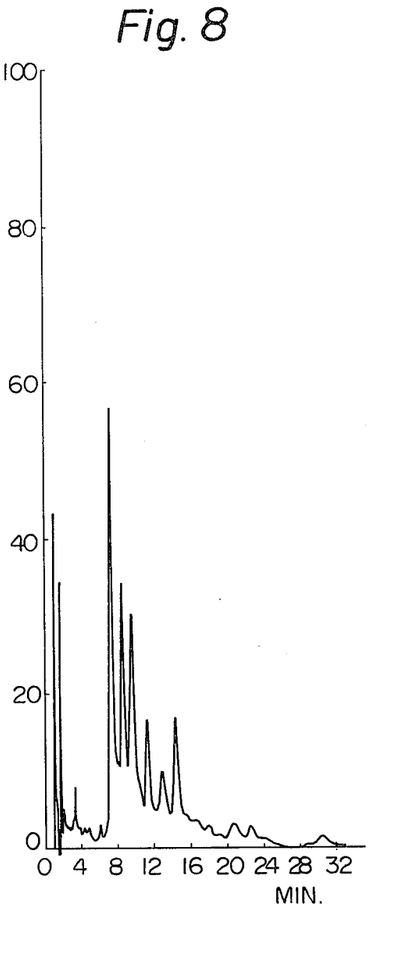
FIG. 8 shows a chromatogram obtained by subjecting the Extract A obtained in Example 3 to analytical HPLC.

While observing elution peaks with a detector, an eluate chosen on the basis of the peak corresponding to Fr-3-1 fraction of FIG. 6 of the accompanying drawings was collected for 12 minutes and concentrated to dryness at 40° C. to yield 0.88 g of a white powder-like Extract B-3. The data obtained by subjecting the thus obtained Extract B-3 to HPLC under the same conditions as in Example 1 is shown in the chart depicted in FIG. 7 of the accompanying drawings.

EXAMPLE 3

In the same manner as the first operation in Example 1, 500 g of finely divided bark of *Marsdenia cundurango* Reichenbach fil. was extracted with chloroform.

All the filtrates were combined and concentrated to dryness at 40° C. under reduced pressure to yield 46 g of an extract. To this extract, there was added 100 ml of methanol, and the mixture was well stirred, and then filtered. The residue with 30 ml of methanol added thereto was treated in the same manner as the above four times. All the filtrates were combined and concentrated to dryness at 45° C. under reduced pressure to yield 24 g of an extract. This extract was dissolved in 50 ml of chloroform added thereto, and then treated as in Example 1 to yield 13 g of a brown powder-like Extract A. The data obtained by subjecting this Extract A to HPLC under the same conditions as in Example 1 is shown in the chart depicted in FIG. 8 of the accompanying drawings.

Then, the Extract A (13 g) was dissolved in 30 ml of chloroform and adsorbed on 80 g of silica gel (Wako-gel C-200 manufactured by Wako Junyaku Industry Co., Ltd., 200 mesh) with which a column (i.d.×1.=3 cm×22 cm) was packed by the dry process.

First, eluates obtained by the elution with 160 ml of chloroform, 200 ml of a mixture of chloroform and methanol (volumetric ratio=97:3) and then 200 ml of a mixture of chloroform and methanol (volumetric ratio=95:5) were discarded, and then an eluate obtained by the elution with 1 l of a mixture of chloroform and methanol (volumetric ratio=93:7) was divided into the first 600 ml fraction and the remaining 400 ml fraction. The first 600 ml fraction was concentrated and then dried at 45° C. under reduced pressure for 6 hours and crushed to yield 4.21 g of an extract.

This extract was dissolved in 40 ml of chloroform followed by the addition of n-hexane in the maximum but no turbidity-causing amount. The resulting solution was subjected to HPLC for mass collection [System 500 manufactured by Waters Co., Ltd.; filler: Preppak 500-Silica (totally porous silica gel manufactured by Waters Co., Ltd., spherical, surface area: 320 m²/g); column: i.d.×1.=57 mm×300 mm, each contains 325 g of the filler; eluant: a mixture of n-hexane/chloroform/methanol (volumetric ratio=6:1:1); flow rate: 150 ml/min.; and detection: at RI ($1/20\times10^{-4}$ RIUFS)]. While observing elution peaks with a detector, an eluate chosen on the basis of the peak corresponding to Fr-2-1 fraction shown in FIG. 3 of the accompanying drawings was collected for six minutes and thirty seconds and another eluate chosen on the basis of the peak corresponding to Fr-2-2 fraction shown in the same drawing was collected for 8 minutes. The respective fractions were concentrated to dryness to yield 0.85 g of a white powder-like Extract B-1 (corres. to Fr-2-1 fraction) and 0.72 g of a white powder-like Extract B-2 (corres. to Fr-2-2 fraction).

Figure 9:
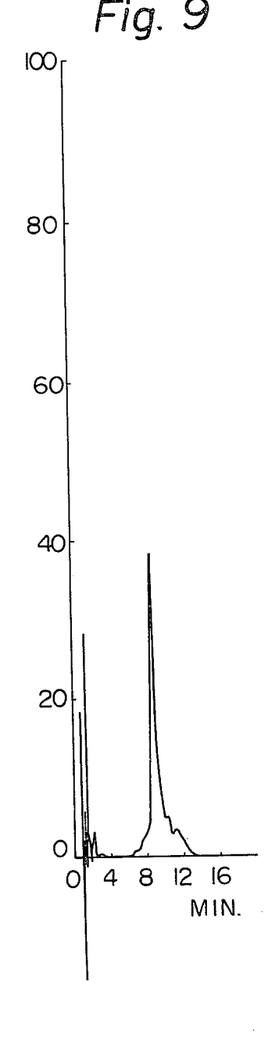
FIG. 9 shows a chromatogram obtained by subjecting the Extract B-1 obtained in Example 3 to analytical HPLC.
Figure 10:
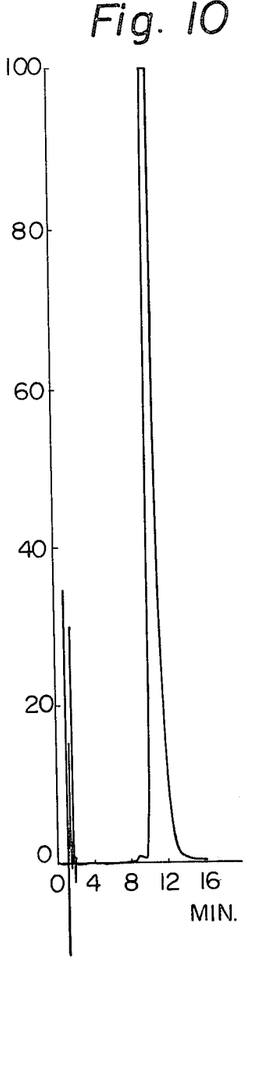
FIG. 10 shows a chromatogram obtained by subjecting the Extract B-2 obtained in Example 3 to analytical HPLC.

The data obtained by subjecting the thus obtained Extracts B-1 and B-2, respectively, to HPLC under the same conditions as in Example 1 is shown in the charts depicted in FIGS. 9 and 10 of the accompanying drawings, respectively.

EXAMPLE 4

Four hundred milliliters of the latter half of the eluate obtained by eluting the content of the silica gel column with the mixture of chloroform and methanol (volumetric ratio=93:7) in Example 3 was concentrated and then dried at 45° C. under reduced pressure for 6 hours and crushed to yield 1.76 g of an extract.

This extract was dissolved in 30 ml of a 70% (v/v) aqueous methanol solution and then subjected to HPLC for mass collection [System 500 manufactured by Waters Co.; Ltd.; filler: Preppak 500-C18 (manufactured by Waters Co., Ltd., chemically bonded type C-18); column: i.d.×1.=57 mm×300 mm); eluant: a 70% (v/v) aqueous methanol solution; flow rate: 100 ml/min.; and detection: at RI ($1/50\times10^{-4}$ RIUFS)]. While observing elution peaks with a detector, an eluate chosen on the basis of the corresponding to Fr-3-1 fraction shown in FIG. 6 of the accompanying drawings was collected for 12 minutes and then concentrated to dryness to yield 0.48 g of a white powder-like Extract B-3.

Figure 11:
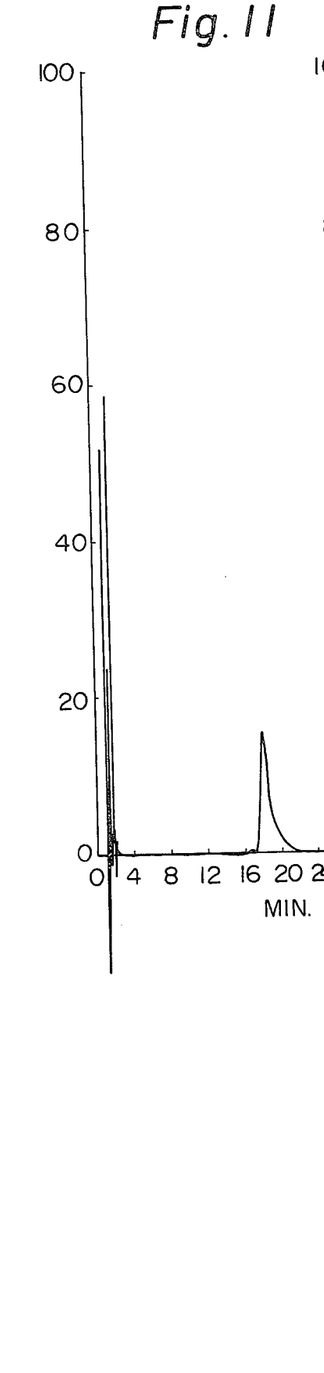
FIG. 11 shows a chromatogram obtained by subjecting the Extract B-3 obtained in Example 4 to analytical HPLC.

The data obtained by subjecting the thus obtained Extract B-3 HPLC under the same conditions as in Example 1 is shown in the chart depicted in FIG. 11 of the accompanying drawings.

EXAMPLE 5

To 40 g of an extract obtained by carrying out the first and second operations as in Example 1, there was added 50 ml of carbon tetrachloride, and the mixture was well stirred and allowed to stand for 12 hours. Then, the mixture was subjected to decantation to obtain the insoluble portion. To this insoluble portion, there was added 25 ml of carbon tetrachloride, and the mixture was well stirred and allowed to stand for 5 hours. The mixture was subjected to decantation to obtain the insoluble portion which was then treated in the same manner as the above two more times. The finally obtained insoluble portion was dried at 45° C. under reduced pressure for 6 hours and crushed to yield 17.4 g of a brown powder-like Extract A.

Figure 12:
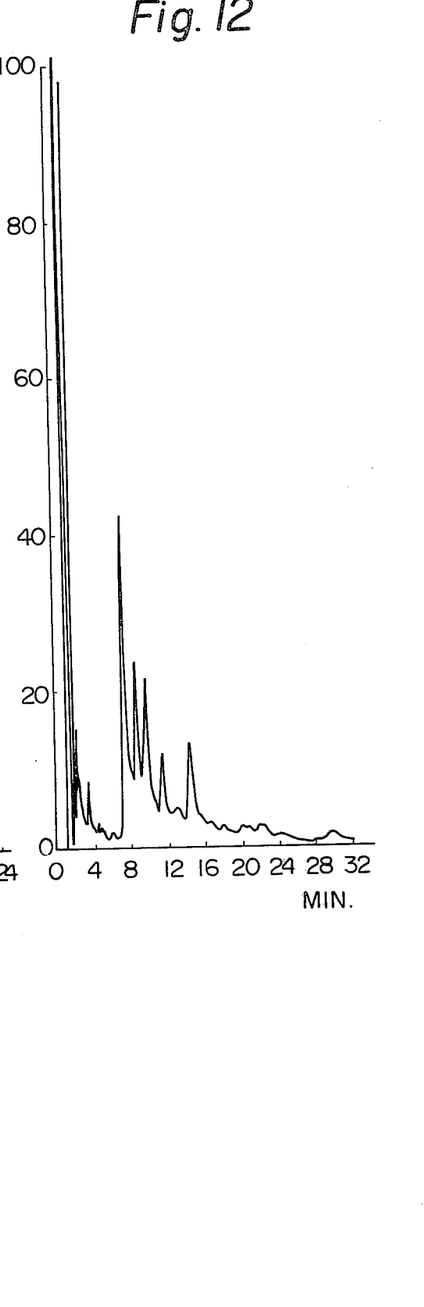
FIG. 12 shows a chromatogram obtained by subjecting the Extract A obtained in Example 5 to analytical HPLC.

The data obtained by subjecting this Extract A to HPLC under the same conditions as in Example 1 is shown in the chart depicted in FIG. 12 of the accompanying drawings.

EXAMPLE 6

In the same manner as in Example 5, but using toluene instead of the carbon tetrachloride in the third operation, there was produced 12.3 g of a brown powder-like Extract A.

Figure 13:
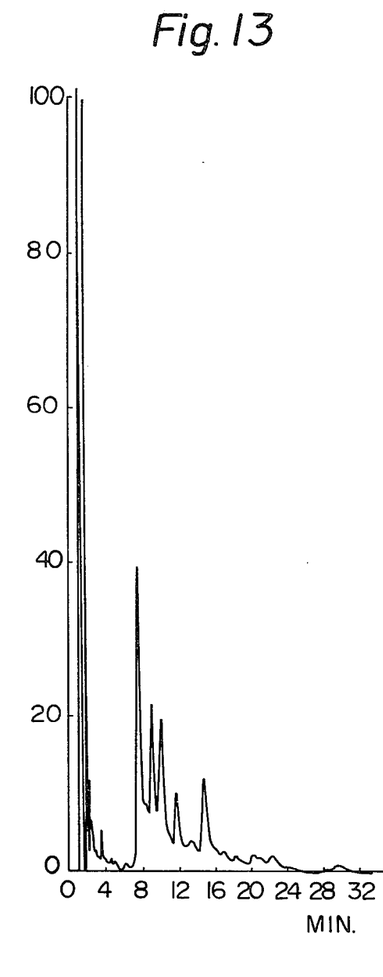
FIG. 13 shows a chromatogram obtained by subjecting the Extract A obtained in Example 6 to analytical HPLC.

The data obtained by subjecting this Extract A to HPLC under the same conditions as in Example 1 is shown in the chart depicted in FIG. 13 of the accompanying drawings.

EXAMPLE 7

In the same manner as in Example 5, but using benzene instead of the carbon tetrachloride in the third operation, there was produced 16.4 g of a brown powder-like Extract A.

Figure 14:
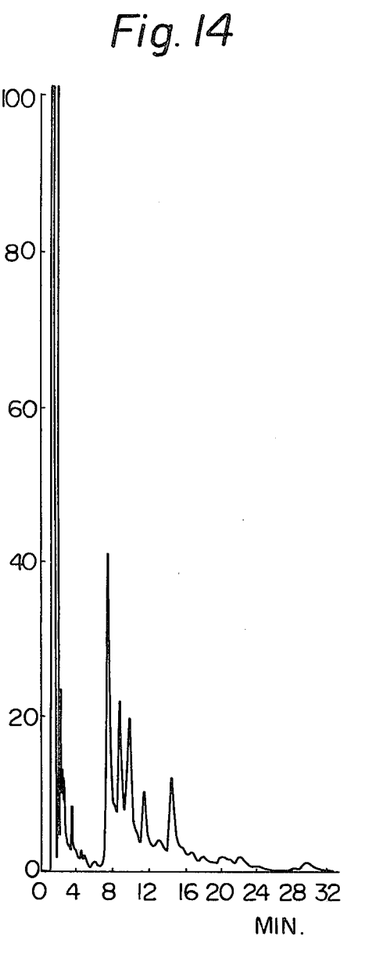
FIG. 14 shows a chromatogram obtained by subjecting the Extract A obtained in Example 7 to analytical HPLC.

The data obtained by subjecting this Extract A to HPLC under the same conditions as in Example 1 is shown in the chart depicted in FIG. 14 of the accompanying drawings.

EXAMPLE 8

In the same manner as the first operation in Example 1,500 g of finely divided bark of *Marsdenia cundurango* Reichenbach fil. was extracted with acetone.

All the filtrates were combined and concentrated to dryness at 40° C. under reduced pressure to yield 43 g of an extract.

To this extract, there was added 100 ml of methanol, and the mixture was well stirred and filtered. The residue with 30 ml of methanol added thereto was treated in the same manner as the above four times. All the filtrates were combined and concentrated to dryness at 45° C. under reduced pressure to yield 22 g of an extract. To this extract, there was added 150 ml of chloroform, and the mixture was well stirred and filtered. The residue with 50 ml of chloroform added thereto was treated in the same manner as the above three times. All the filtrates were combined and subjected to suction filtration using Fibra Cel BH-40 (Johns Manville Co., Ltd.) as the filtration aid, and the resulting filtrate was concentrated to dryness at 40° C. under reduced pressure to yield 20 g of an extract. This extract was dissolved in 50 ml of chloroform added thereto and then worked up as in Example 1 to yield 11.3 g of a brown powder-like Extract A.

Figure 15:
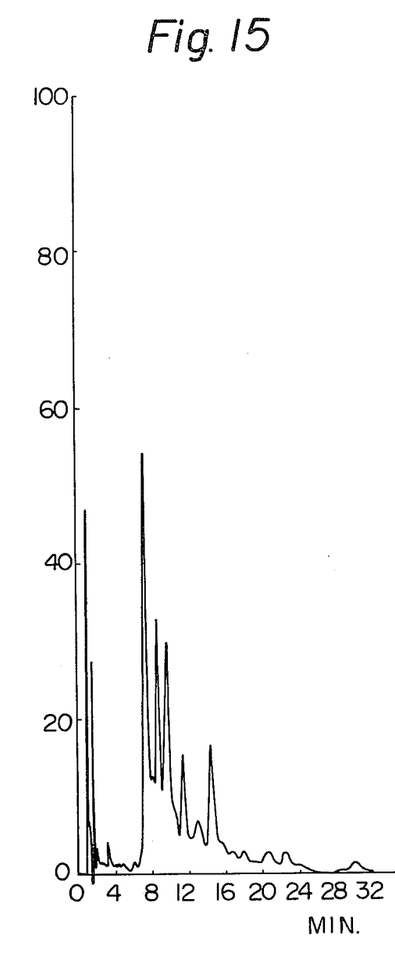
FIG. 15 shows a chromatogram obtained by subjecting the Extract A obtained in Example 8 to analytical HPLC.

The data obtained by subjecting this Extract A to HPLC under the same conditions as in Example 1 is shown in the chart depicted FIG. 15 of the accompanying drawings.

EXAMPLE 9

In the same manner as the first operation in Example 1,500 g of finely divided bark of *Marsdenia cundurango* Reichenbach fil. was extracted with ethyl acetate. All the filtrates were combined and concentrated to dryness at 45° C. under reduced pressure to yield 38 g of an extract. This extract with 100 ml of methanol added thereto was treated in the same manner as in Example 8 to yield 15.8 g of a brown powder-like Extract A.

Figure 16:
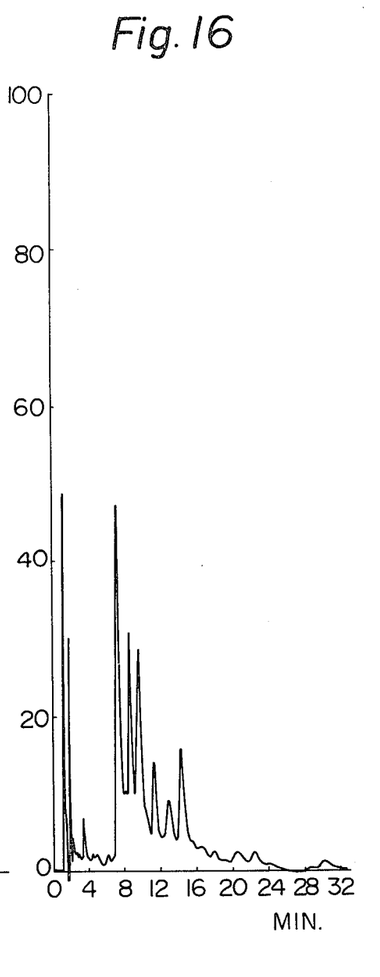
FIG. 16 shows a chromatogram obtained by subjecting the Extract A obtained in Example 9 to analytical HPLC.

The data obtained by subjecting this Extract A to HPLC under the same conditions as in Example 1 is shown in the chart depicted in FIG. 16 of the accompanying drawings.

EXAMPLE 10

In the same manner as the first operation in example 1,500 g of finely divided bark of *Marsdenia cundurango* Reichanbach fil. was extracted with dioxane.

All the filtrates were combined and concentrated to dryness at 50° C. under reduced pressure to yield 60 g of an Extract.

To this extract, there was added 100 ml of methanol, and then the mixture was treated as in Example 8 to yield 16 g of a brown powder-like Extract A.

Figure 17:
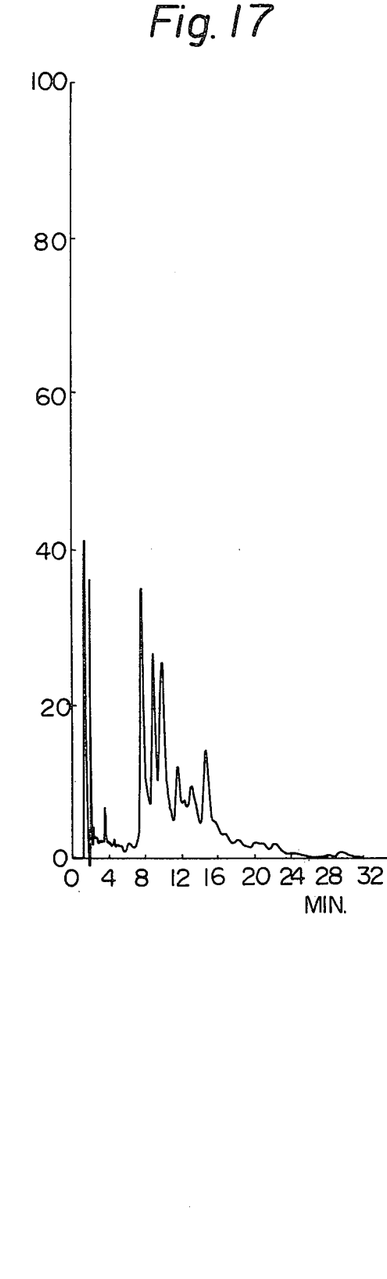
FIG. 17 shows a chromatogram obtained by subjecting the Extract A obtained in Example 10 to analytical HPLC.

The data obtained by subjecting this Extract A to HPLC under the same conditions as in Example 1 is shown in the chart depicted in FIG. 17 of the accompanying drawings.

EXAMPLE 11

To 500 g of finely divided bark of *Marsdenia cundurango* Reichenbach fil., there was added 2.5 l of hot water followed by well stirring. The mixture was allowed to stand at room temperature overnight. The mixture was filtered, and the residue was treated in the same manner as the above four times, but each time using 1 l of hot water. All the filtrates were combined and concentrated to dryness at 50° C. under reduced pressure to yield 94 g of an extract.

To this extract, there was added 300 ml of methanol, and the mixture was well stirred and filtered. The residue with 100 ml of methanol added thereto was treated in the same manner as the above four times. All the filtrates were combined and concentrated to dryness at 45° C. under reduced pressure to yield 53 g of an extract.

To this extract transferred into a separatory funnel, there was added 150 ml of chloroform, and the mixture was then treated in the same manner as in Example 1 to yield 5.6 g of a brown powder-like Extract A.

Figure 18:
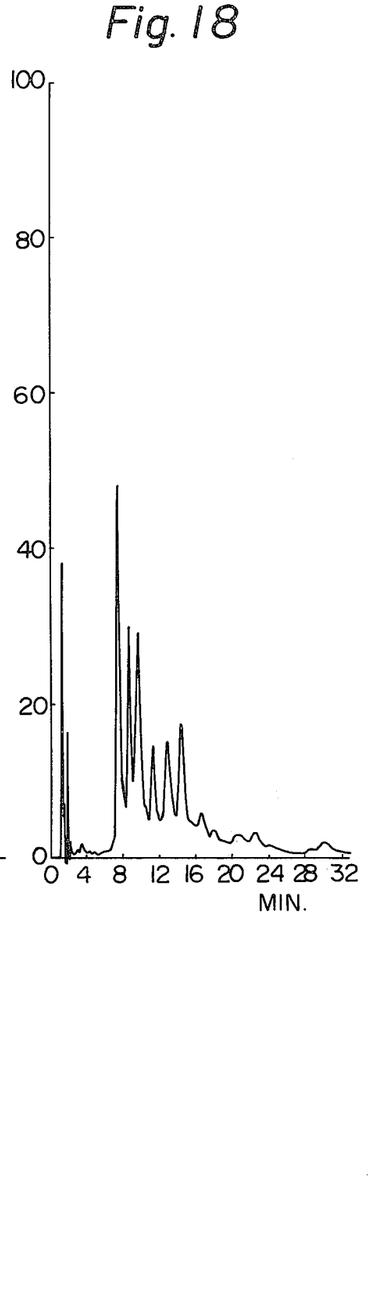
FIG. 18 shows a chromatogram obtained by subjecting the Extract A obtained in Example 11 to analytical HPLC.

The data obtained by subjecting this Extract A to HPLC under the same conditions as in Example 1 is shown in the chart depicted in FIG. 18 of the accompanying drawings.

EXAMPLE 12

Finely divided bark of *Marsdenia cundurango* Reichenbach fil. (500 g) was heated in an autoclave at 120° C. for 30 minutes followed by the addition of 2 l of water, and then the mixture was allowed to stand at room temperature overnight. Then, the mixture was filtered, and the residue with 1 l of water added thereto was then treated in the same manner as the above four times. All the filtrates were combined and concentrated to dryness at 50° C. under reduced pressure to yield 96 g of an extract. Then, the mixture was treated in the same manner as in Example 11 to yield 6.8 g of a brown powder-like Extract A.

Figure 19:
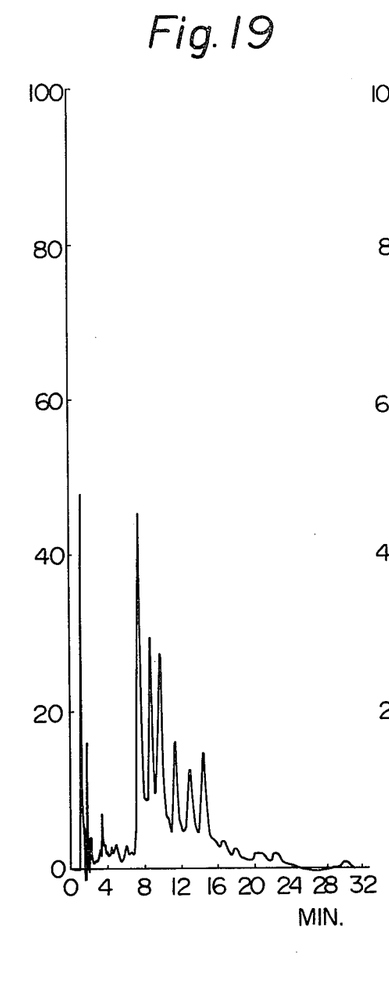
FIG. 19 shows a chromatogram obtained by subjecting the Extract A obtained in Example 12 to analytical HPLC.

The data obtained by subjecting this Extract A to HPLC under the same conditions as in Example 1 is shown in the chart depicted in FIG. 19 of the accompanying drawings.

EXAMPLE 13

Finely divided bark of *Marsdenia cundurango* Reichenbach fil. (500 g) was heated in an autoclave at 120° C. for 30 minutes followed by the addition of 1.5 l of a 50% (v/v) aqueous methanol solution, and the mixture was allowed to stand at room temperature overnight. Then, the mixture was filtered, and the residue with 0.75 l of a 50% (v/v) aqueous methanol solution added thereto was treated in the same manner as the above four times. All the filtrates were combined and concentrated to dryness at 50° C. under reduced pressure to yield 103 g of an extract. Then, the mixture was worked up as in Example 11 to yield 9 g of a brown powder-like Extract A.

Figure 20:
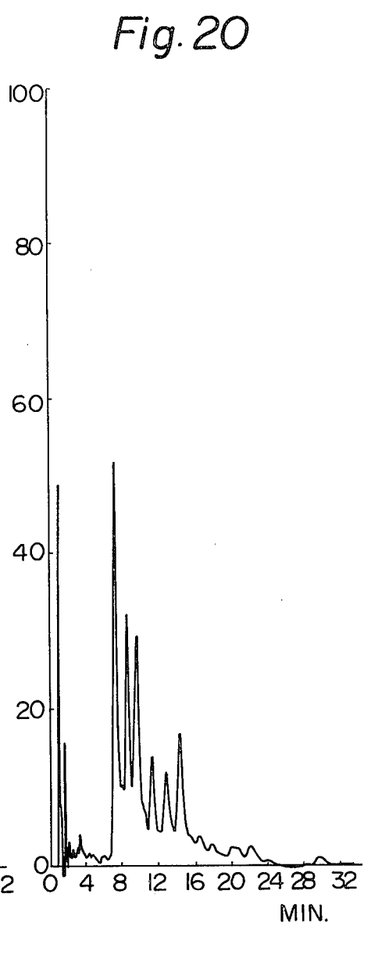
FIG. 20 shows a chromatogram obtained by subjecting the Extract A obtained in Example 13 to analytical HPLC.

The data obtained by subjecting this Extract A to HPLC under the same conditions as in Example 1 is shown in the chart depicted in FIG. 20 of the accompanying drawings.

What is claimed is:

1. An extract of *Marsdenia cundurango* Reichenbach fil. which is soluble in $C_{1-3}$ lower alcohols and in chloroform and dichloromethane and insoluble in pentane, hexane, heptane, carbon tetrachloride, toluene and benzene, and shows the chromatogram depicted in FIG. 4 of the acompanying drawings when subjected to analytical HPLC in which the filler is totally porous crushed type silica gel. $5\mu$; the column has an i.d. of 4 mm and a length of 200 mm; the eluent is a mixture of n-hexane/chloroform/methanol having a volumetric ratio of 7:2:1; the flow rate is 1.5 ml/min.; the pressure is 30 kg/cm$^2$; and detection is at U.V. 280 nm.

2. An extract of *Marsdenia cundurango* Reichenbach fil. which is soluble in C$_{1-3}$ lower alcohols and in chloroform and dichloromethane and insoluble in pentane, hexane, heptane, carbon tetrachloride, toluene and benzene, and shows the chromatogram depicted in FIG. 5 of the accompanying drawings when subjected to analytical HPLC in which the filler is (totally porous crushed type silica gel, $5\mu$; the column has an i.d. of 4 mm and a length of 200 mm; the eluent is a mixture of n-hexane/chloroform/methanol having a volumetric ratio of 7:2:1; the flow rate is 1.5 ml/min.; the pressure is 30 kg/cm$^2$; and detection is at U.V. 280 nm, 0.64 AUFS.

3. An extract of *Marsdenia cundurango* Reichenbach fil. which is soluble in C$_{1-3}$ lower alcohols and in chloroform and dichloromethane and insoluble in pentane, hexane, heptane, carbon tetrachloride, toluene and benzene, and shows the chromatogram depicted in FIG. 7 of the acompanying drawings when subjected to analytical HPLC in which the filler is totally porous crushed type silica gel, $5\mu$; the column has an i.d. of 4 mm and a length of 200 mm, the eluent is a mixture of n-hexane/chloroform/methanol having a volumetric ratio of 7:2:1; the flow rate is 1.5 ml/min.; the pressure is 30 kg/cm$^2$; and detection is at U.V. 280 nm, 0.64 AUFS.

4. A process for preparing an extract of *Marsdenia cundurango* Reichenbach fil., comprising treating *Marsdenia cundurango* Reichenbach fil. with the following three types of solvents in an optional order:
(1) a C$_{1-3}$ lower alcohol for collecting the portion which is soluble therein;
(2) chloroform or dichloromethane for collecting the portion which is soluble therein; and
(3) carbon tetrachloride, toluene or benzene for removing the portion which is soluble therein.

5. A process for preparing the extract in accordance with claim 1, comprising:
treating *Marsdenia cundurango* Reichenbach fil. with the following three types of solvents in a optional order:
(1) a C$_{1-3}$ lower alcohol for collecting the portion which is soluble therein;
(2) chloroform or dichloromethane for collecting the portion which is soluble therein; and
(3) pentane, hexane, heptane, carbon tetrachloride, toluene or benzene for removing the portion which is soluble therein, to yield an extract of *Marsdenia cundurango* Reichenbach fil.;
subjecting the above extract to analytical HPLC in which the filler is totally porous spherical silica gel having a surface area of 320 m$^2$/g; the column has an i.d. of 57 mm and a length of 300 mm; the eluant is a mixture of n-hexane/chloroform/methanol having a volumetric ratio of 6:3:1; the flow rate is 150 ml/min.; and detection is at RI, $1/20 \times 10^{-4}$ RIUFS, to collect the elution fraction chosen on the basis of the peak corresponding to the Fr-2 fraction depicted in FIG. 2 of the accompanying drawings; and
subjecting said elution fraction to analytical HPLC under the same conditions as the above except that another mixture of n-hexane/chloroform/methanol having a volumetric ratio of 6:1:1 is used as the eluant to collect the elution fraction chosen on the basis of the peak corresponding to the Fr-2-1 fraction depicted in FIG. 3 of the accompanying drawings.

6. A process for preparing the extract in accordance with claim 2, comprising:
treating *Marsdenia cundurango* Reichenbach fil. with the following three types of solvents in an optional order:
(1) a C$_{1-3}$ lower alcohol for collecting the portion which is soluble therein;
(2) chloroform or dichloromethane for collecting the portion which is soluble therein; and
(3) pentane, hexane, heptane, carbon tetrachloride, toluene or benzene for removing the portion which is soluble therein, to yield an extract of *Marsdenia cundurango* Reichenbach fil.;
subjecting the above extract to analytical HPLC in which the filler is totally porous spherical silica gel having a surface area of 320 m$^2$/g; the column has an i.d. of 57 mm and a length of 300 mm; the eluant is a mixture of n-hexane/chloroform/methanol having a volumetric ratio of 6:3:1; the flow rate is 150 ml/min.; and detection is at RI, $1/20 \times 10^{-4}$ RIUFS to collect the elution fraction chosen on the basis of the peak corresponding to the Fr-2 fraction depicted in FIG. 2 of the accompanying drawings; and
subjecting said elution fraction to analytical HPLC under the same conditions as the above except that another mixture of n-hexane/chloroform/methanol having a volumetric ratio of 6:1:1 is used as the eluant to collect the elution fraction chosen on the basis of the peak corresponding to the Fr-2-2 fraction depicted in FIG. 3 of the accompanying drawings.

7. A process for preparing the extract in accordance with claim 3, comprising:
treating *Marsdenia cundurango* Reichenbach fil with the following three types of solvents in an optional order:
(1) a C$_{1-3}$ lower alcohol for collecting the portion which is soluble therein;
(2) chloroform or dichloromethane for collecting the portion which is soluble therein; and
(3) pentane, hexane, heptane, carbon tetrachloride, toluene or benzene for removing the portion which is soluble therein, to yield an extract of *Marsdenia cundurango* Reichenbach fil.;
subjecting the above extract to analytical HPLC in which the filler is totally porous spherical silica gel having a surface area of 320 m$^2$/g; the column has an i.d. of 57 mm and a length of 300 mm; the eluant is a mixture of n-hexane/chloroform/methanol having a volumetric ratio of 6:3:1; the flow rate is 150 ml/min.; and detection is at RI, $1/20 \times 10^{-4}$ RIUFS, to collect the elution fraction chosen on the basis of the peak corresponding to the Fr-3 fraction depicted in FIG. 2 of the accompanying drawings; and
subjecting said elution portion to analytical HPLC in which the filler is chemically bonded type C-18;

the column has an i.d. of 57 mm and a length of 300 mm; the eluant is a 70% (v/v) aqueous methanol solution; the flow rate is 100 ml/min.; and detection is at RI, $1/50 \times 10^{-4}$ RIUFS, to collect the elution fraction chosen on the basis of the peak corresponding to the Fr-3-1 fraction depicted in FIG. 6 of the accompanying drawings.

Figure 3:
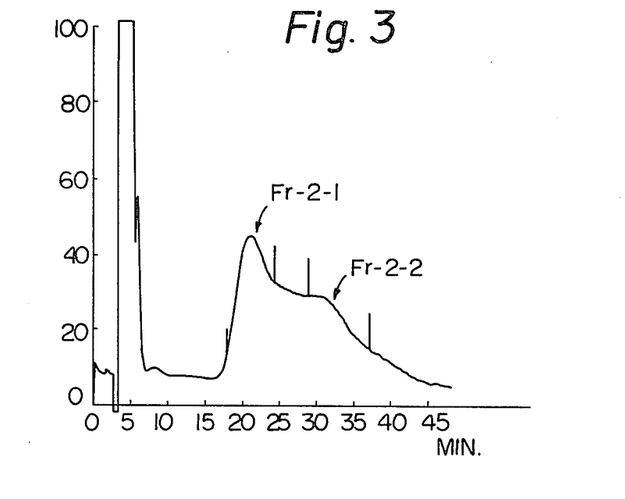
FIG. 3 shows a chromatogram obtained by subjecting the Fr-2 fraction depicted in FIG. 2 to HPLC for mass collection.
Figure 4:
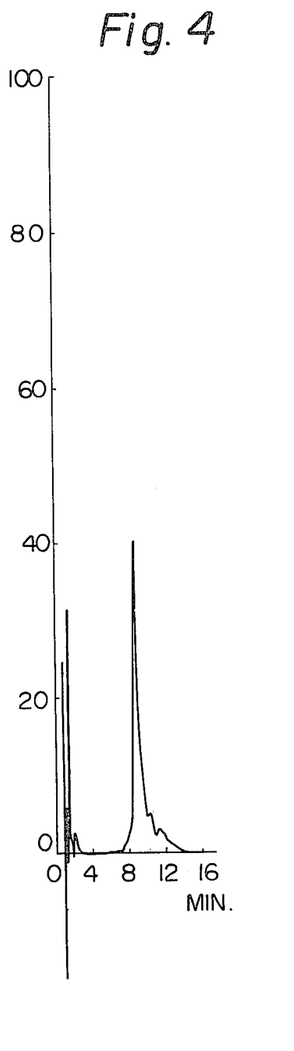
FIG. 4 shows a chromatogram obtained by subjecting the Extract B-1 obtained in Example 1 to analytical HPLC.

8. A process for preparing the extract in accordance with claim 1, comprising:

treating *Marsdenia cundurango* Reichenbach fil. with the following three types of solvents in an optional order:
(1) a $C_{1-3}$ lower alcohol for collecting the portion which is soluble therein;
(2) chloroform or dichloromethane for collecting the portion which is soluble therein; and
(3) pentane, hexane, heptane, carbon tetrachloride, toluene or benzene for removing the portion which is soluble therein, to yield an extract of *Marsdenia cundurango* Reichenbach fil.;

subjecting the above extract to elution on silica gel by the open column method with chloroform and a mixture of chloroform and methanol, having volumetric ratios of 97:3 and 95:5, to remove the portion which is soluble therein and then eluting with a mixture of chloroform and methanol having a volumetric ratio of 93:7 and collecting the first half of the elution fraction; and subjecting said elution fraction to analytical HPLC in which the filler is totally porous, spherical silica gel having a surface area of 320 m²/g; the column has an i.d. of 57 mm and a length of 300 mm; the eluant is a mixture of n-hexane/chloroform/methanol having a volumetric ratio of 6:1:1; the flow rate is 150 ml/min; and detection is at RI, $1/20 \times 10^{-4}$ RIUFS, to collect the elution fraction chosen on the basis of the peak corresponding to the Fr-2-1 fraction depicted in FIG. 3 of the accompanying drawings.

9. A process for preparing the extract in accordance with claim 2, comprising:

treating *Marsdenia cundurango* Reichenbach fil. with the following three types of solvents in an optional order:
(1) a $C_{1-3}$ lower alcohol for collecting the portion which is soluble therein;
(2) chloroform or dichloromethane for collecting the portion which is soluble therein; and
(3) pentane, hexane, heptane, carbon tetrachloride, toluene or benzene for removing the portion which is soluble therein, to yield an extract of *Marsdenia cundurango* Reichenbach fil.;

subjecting the above extract to elution on silica gel by the open column method with chloroform and a mixture of chloroform and methanol, having volumetric ratios 97:3 and 95:5, to remove the portion which is soluble therein and then eluting with a mixture of chloroform and methanol having a volumetric ratio of 93:7 and collecting the first half of the elution fraction; and subjecting said elution fraction to analytical HPLC in which the filler is totally porous, spherical silica gel having a surface area of 320 m²/g; the column has an i.d. of 57 mm and a length of 300 mm; the eluant is a mixture of n-hexane/chloroform/methanol having a volumetric ratio of 6:1:1; the flow rate is 150 ml/min; and detection is at RI, $1/20 \times 10^{-4}$ RIUFS, to collect the elution fraction chosen on the basis of the peak corresponding to the Fr-2-2 fraction depicted in FIG. 3 of the accompanying drawings.

10. A process for preparing the extract in accordance with claim 3, comprising:

treating *Marsdenia cundurango* Reichenbach fil. with the following three types of solvents in an optional order:
(1) a $C_{1-3}$ lower alcohol for collecting the portion which is soluble therein;
(2) chloroform or dichloromethane for collecting the portion which is soluble therein; and
(3) pentane, hexane, heptane, carbon tetrachloride, toluene or benzene for removing the portion which is soluble therein, to yield an extract of *Marsdenia cundurango* Reichenbach fil.;

subjecting the above extract to elution on silica gel by the open column method with chloroform and a mixture of chloroform and methanol, having volumetric ratios of 97:3 and 95:5, to remove the portion which is soluble therein and then eluting with a mixture of chloroform and methanol having a volumetric ratio of 93:7 and collecting the latter half of the elution fraction; and subjecting said elution portion to analytical HPLC in which the filler is chemically bonded type C-18; the column has an i.d. of 57 mm and a length of 300 mm; the eluant is a 70% (v/v) aqueous methanol solution; the flow rate is 100 ml/min.; and detection is at RI, $1/50 \times 10^{-4}$ RIUFS, to collect the elution fraction chosen on the basis of the peak corresponding to the Fr-3-1 fraction depicted in FIG. 6 of the accompanying drawings.

11. A process as described in any one of claims 4–7 or 8–10, wherein said starting material is the extract obtained by extracting *Marsdenia cundurango* Reichenbach fil. with an aliphatic ketone, a lower aliphatic ester or ether, or hot water, or with water or an aqueous lower alcohol after the direct treatment with heat at 110°–130° C. for 30 minutes.

12. A pharmaceutical composition characterized by containing the extract of *Marsdenia cundurango* Reichenbach fil. as described in any one of claims 1–3 in an amount effective against Sarcoma-180 and Ehrlich carcinoma tumors, with a pharmaceutically acceptable diluent or carrier.

13. A method of treating Sarcoma-180 or *Ehrlich carcinoma* tumor in a living animal body comprising administering an effective amount of the extract of *Marsdenia cundurango* Reichenbach fil. as described in any one of claims 1–3 to the body.

* * * * *